United States Patent [19]
Griesinger et al.

[11] Patent Number: 6,097,295
[45] Date of Patent: Aug. 1, 2000

[54] APPARATUS FOR DETERMINING THE ALERTNESS OF A DRIVER

[75] Inventors: Manfred Griesinger, Leonberg; Goetz Renner, Esslingen; Walter Ziegler, Stuttgart, all of Germany

[73] Assignee: DaimlerChrysler AG, Stuttgart, Germany

[21] Appl. No.: 09/238,141

[22] Filed: Jan. 28, 1999

[30] Foreign Application Priority Data

Jan. 28, 1998 [DE] Germany ............................ 198 03 158

[51] Int. Cl.⁷ ............................................. G08B 23/00
[52] U.S. Cl. ............................................ 340/576; 382/117
[58] Field of Search .................................. 340/575, 576, 340/573.1, 600, 693.6; 351/209, 205; 600/558; 382/118, 117

[56] References Cited

U.S. PATENT DOCUMENTS

| | | | |
|---|---|---|---|
| 3,966,310 | 6/1976 | Larson | 351/16 |
| 4,359,724 | 11/1982 | Zimmerman et al. | 340/575 |
| 4,725,824 | 2/1988 | Yoshioka | 340/575 |
| 4,755,043 | 7/1988 | Carter | 351/205 |
| 4,850,691 | 7/1989 | Gardner et al. | 351/221 |
| 5,187,506 | 2/1993 | Carter | 351/221 |
| 5,204,703 | 4/1993 | Hutchinson et al. | 351/210 |
| 5,402,109 | 3/1995 | Mannik | 340/575 |
| 5,566,067 | 10/1996 | Hobson et al. | 364/419.2 |
| 5,573,006 | 11/1996 | Shimotani et al. | 128/745 |
| 5,682,144 | 10/1997 | Mannik | 340/575 |
| 5,786,765 | 7/1998 | Kumakura et al. | 340/576 |
| 5,805,720 | 9/1998 | Suenaga et al. | 382/117 |
| 5,867,587 | 2/1999 | Aboutalib et al. | 382/117 |
| 5,878,156 | 3/1999 | Okumura | 382/118 |
| 5,909,179 | 6/1999 | Hiltman | 340/573.1 |

FOREIGN PATENT DOCUMENTS

| | | |
|---|---|---|
| 35 41 726 A1 | 5/1987 | Germany . |
| 41 40 160 A1 | 6/1993 | Germany . |
| 44 19 489 A1 | 12/1995 | Germany . |
| 196 21 435 A1 | 12/1996 | Germany . |
| 197 15 519 A1 | 11/1997 | Germany . |
| 6-270711 | of 1994 | Japan . |
| 7-061256 | of 1995 | Japan . |

OTHER PUBLICATIONS

B. Wilhelm, H. Wilhelm, "Die Pupille als Schlaf–Wach–Indikator" in Z. prakt. Augenheilkd. 15, 1994, pp. 185–189.

I.E. Loewenfeld, "The Pupil," vol. I, Wayne State University Press, Detroit, 1993.

*Primary Examiner*—Jeffery A. Hofsass
*Assistant Examiner*—Anh V. La
*Attorney, Agent, or Firm*—Evenson, McKeown, Edwards & Lenahan, P.L.L.C.

[57] ABSTRACT

An apparatus for determining the alertness of a person, especially a vehicle or machine operator, comprises an image pickup system for recording images of the area of at least one eye of the person, and an image evaluating system which evaluates the images detected by the image pickup system and contains means for detecting the shutting of an eye. The image evaluating system has means for determining pupil size and an evaluating apparatus which determines the alertness according to the eye closing state information obtained by the closed-eye detection means, and according to the pupil size information obtained by the pupil size determining means, with classification into one of at least three stages. The apparatus is used, for example, for determining the alertness of drivers of motor vehicles.

18 Claims, 2 Drawing Sheets

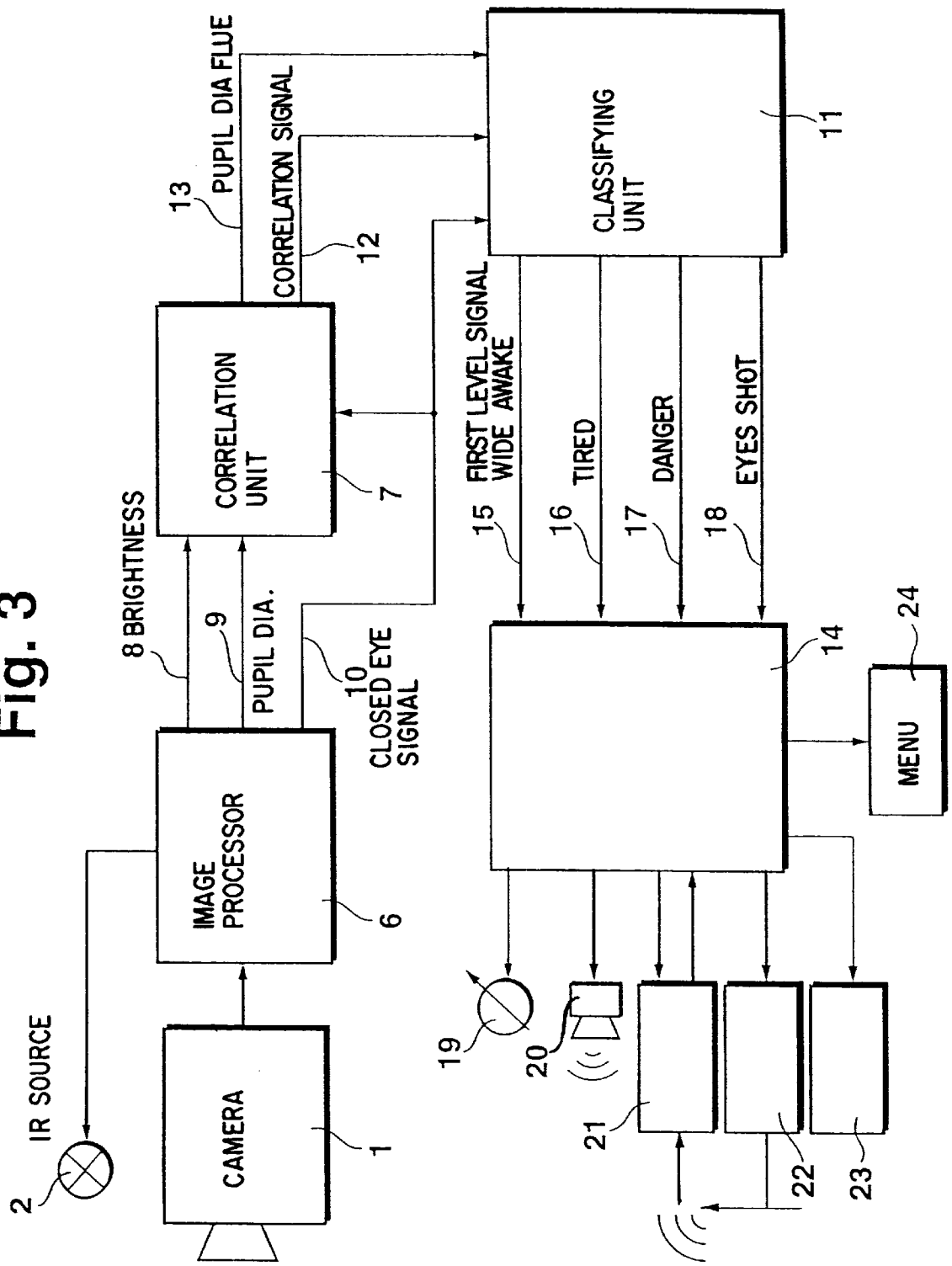

APPARATUS FOR DETERMINING THE ALERTNESS OF A DRIVER

BACKGROUND AND SUMMARY OF THE INVENTION

This application claims the priority of German Application No. 198 03 158.0, filed Jan. 28, 1998, the disclosure of which is expressly incorporated by reference herein.

The invention relates to an apparatus for determining the alertness of a person, especially a person operating a motor vehicle or machine, having an imaging system for imaging the area of at least one eye of the person, and an image evaluating system which contains eye closing detection means and serves to evaluate the images detected by the imaging system. Such an apparatus serves, for example, to continually monitor the alertness of a driver and to warn him while he is driving and before he falls asleep. For this purpose, pictures of the area of at least one eye are taken by the image pickup system and analyzed by an image evaluating system.

German patent applications DE 196 21 435 A1 and DE 197 15 519 A1, as well as in U.S. Pat. Nos. 4,359,724, 5,402,109 and 5,566,067 disclose an apparatus of this kind. The image evaluating system contains means for recognizing the closing of the eye, whereby any increase in the length of the closing of the eyes is interpreted as an increase of fatigue.

In the system disclosed in DE 196 21 435 A1, the ability to measure pupil movement can also be provided (especially the speed of the pupil). This is used as an additional parameter for the decision as to whether the observed person is awake or sleepy. In the system disclosed in DE 197 15 519 A1, by which the sleepiness of a driver is to be estimated, in an initial period of time after the vehicle is started, a frequency distribution of the blink time of the eye of the driver is established. From this frequency distribution, a threshold value is derived, which is then used in an adjoining, second period of time for judging the degree of sleepiness of the driver. From this, a threshold value is derived which is then employed in a directly following second period of time for judging the degree of sleepiness. This procedure is intended to compensate for differences in the blink period and blink frequency in different people. Here, after starting the vehicle, it is assumed that the driver has a low level of drowsiness.

Picture taking and evaluating systems having means for determining pupil diameter and/or eye movement (i.e., pupil movement) are known from the science of pupillography. They are used in eye research for detecting a pupil's diameter and movements of the eyes. Systems of this kind are disclosed in German patent applications DE 35 41 726 A1, DE 44 19 489 A1 and DE 41 40 160 A1 U.S. Pat. Nos. 3,966,310, 4,755,043, 4,850,691, 5,187,506 and 5,204,703.

Furthermore, it is known that fatigue can be detected from the variation of the pupil's diameter. Studies show especially that, with increasing fatigue the pupils at first narrow, even if the ambient brightness is not especially great, and then fluctuations of the diameter of the pupils occur. This indicates the feasibility of using pupillography to identify persons who are in danger of falling asleep, for example, during road, sea and air travel; see B. Wilhelm, H. Wilhelm, "Die Pupille als Schlaf-Wach-Indikator" in Z. prakt. Augenheilkd. 15, 1994, pages 185, and I. E. Loewenfeld, "The Pupil," vol. I, Wayne State University Press, Detroit, 1993.

The object of the present invention is to provide an alertness detecting apparatus, whereby the wakefulness or alertness of a person (especially the operator of a motor vehicle or of machinery) can be especially reliably determined in order to produce therefrom appropriate responses, e.g., issuance of a timely warning or placing the system being steered or operated by the person into a harmless state.

This and other objects and advantages are achieved by an alertness detecting apparatus having an imaging system for imaging the area of at least one eye of the person, and an image evaluating system which contains eye closing detection means and serves to evaluate the images detected by the imaging system. In this apparatus, the image evaluating system has, in addition to eyelid analyzing means, means for determining pupil diameter as well as an evaluation system which determines alertness in accordance with the closed-eye information obtained by the closed-eye detection means. Once the pupil diameter information is obtained by the pupil diameter determining means, the detected alertness of the driver is classified accordingly into one of at least three stages. Due to the presence of both the closed eye detection means and the pupil diameter determining means, a certain redundancy is achieved, as well as a high reliability in the determination of the state of alertness. Classifying the driver's state of alertness in three or more levels creates the possibility of reacting in stages to incipient fatigue of the person being observed.

In an embodiment of the apparatus according to the invention, the image evaluating system contains means for determining the ambient brightness, and the evaluating system has a correlation unit by which it is possible to determine the degree of correlation of the size of the pupil with the ambient brightness. In this manner, changes in pupil diameter due to fluctuations of the ambient brightness can be accurately distinguished from pupil diameter variations due to the level of alertness.

An embodiment of the apparatus is designed such that, with the multi-stage determination of alertness, it will regard the state of alertness to be highest (i.e., the wide-awake state) if that state is indicated both by a brief closing of the eye, a comparatively high closed-eye frequency and the absence of pupil size variations which do not correlate with the ambient light. On the other hand, the presence of the lowest state of alertness (i.e., the highest degree of fatigue) is assumed whenever the observed duration of the closed-eye times are excessively long.

An embodiment of the apparatus permits an at least four-step determination of alertness. Here, in addition to the stages of highest and lowest alertness, a first intermediate stage of greater alertness and a second intermediate state of lower alertness are defined. These are defined according to whether the measured pupil size fluctuations are below (in one case) and above (in the other case) an appropriate threshold value, and furthermore at least one of the conditions is fulfilled. These conditions are that the pupil size fluctuations do not correlate well with ambient light fluctuations, or the closed-eye duration is in a middle range, or the blinking frequency is below an appropriate threshold value. This achieves a very sensitively graded recognition of fatigue.

An embodiment of the apparatus according to the invention contains a warning unit, actuated by the image evaluation system, which emits warning signals which correspond to the alertness level (locally), especially to the person being observed, or also transmits a signal to a point remote from the person being observed. The transmission can occur from a vehicle to a central station or to other vehicles, for example.

In an embodiment of the apparatus according to the invention, a warning unit is provided which operates a vehicle or machine control system according to the degree of alertness detected. This occurs in such a way that, when a sufficiently low alertness of the person being observed is detected, the vehicle being driven or the machine being operated by the driver will be brought by the control system to a safe operating state. This actively forestalls accidents in the case of vehicles that might be due to driver fatigue, for example, by safely slowing the vehicle or bringing it to a stop through an automatic vehicle driving system activated by the warning unit.

In an embodiment of the apparatus according to the invention, upon recognition of a sufficiently low state of alertness, a warning unit causes an operating unit to give the person under observation an alertness test. Other system reactions can then be made to depend on the proper execution of the alertness test.

Other objects, advantages and novel features of the present invention will become apparent from the following detailed description of the invention when considered in conjunction with the accompanying drawings.

BRIEF DESCRIPTION OF THE DRAWINGS

FIG. 3 is a block diagram of the alertness measuring apparatus which belongs to the image pickup system of FIG. 1.

DETAILED DESCRIPTION OF THE DRAWINGS

Figure 1:
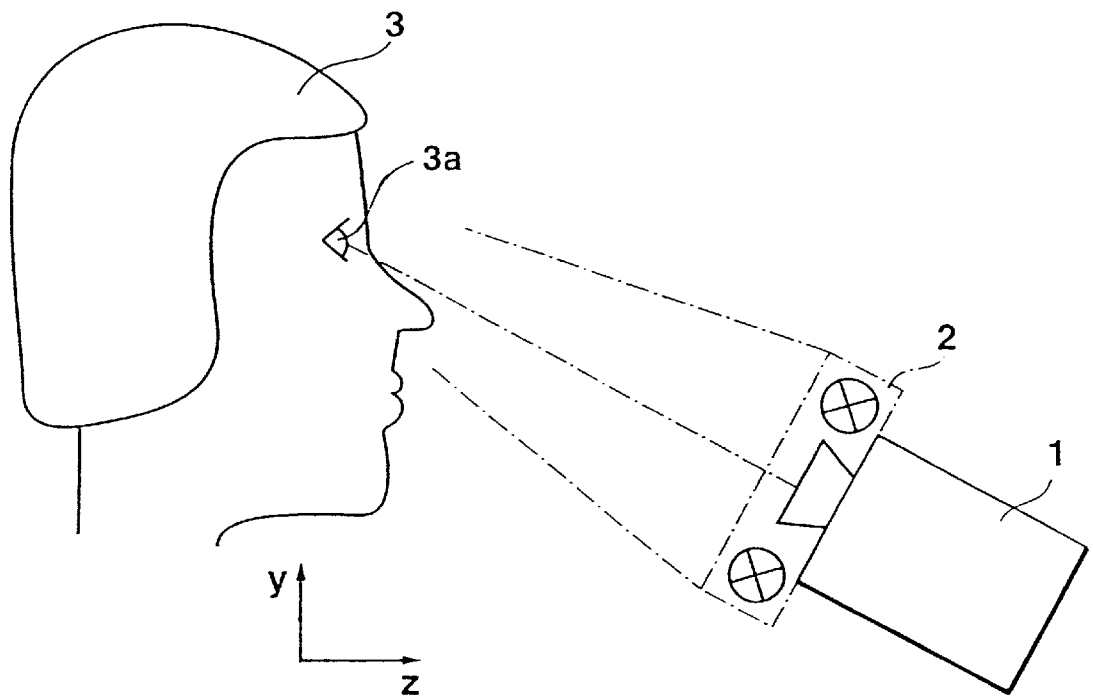
FIG. 1 is a schematic side view of an image pickup system of an alertness measuring system, which is associated with a person being observed.
Figure 2:
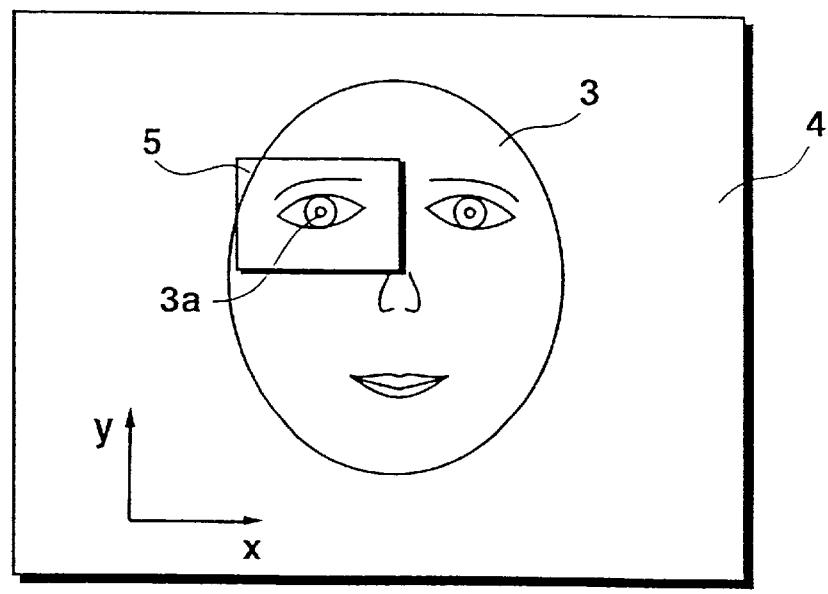
FIG. 2 is a schematic representation of the image frame of the image pickup system of FIG. 1.

The alertness measuring apparatus, as shown in FIGS. 1 and 2, has an optical image pickup system in the form of a camera 1 and an infrared lighting device 2. The lighting device 2 very closely surrounds the optical axis of the camera 1 and serves to produce an outstanding image (as brightly as possible, regardless of the ambient light) of the retina of an eye 3a of an operator 3 of a vehicle or machine.

The focal point of camera 1 and lighting system 2 is chosen such that the observed eye 3a (the right eye in the example shown) will always appear in the camera's field of view 4, will always fall on a photosensitive CCD array of the camera and will do so even while allowing a certain necessary freedom of movement of the head of the person 3 in the xy plane of an indicated xyz system of coordinates.

The camera is designed as a CCD video camera, for example. Furthermore, the diaphragm aperture and focus of the camera 1 are selected such that, despite a certain necessary freedom of movement of the head of the person 3 in the z direction, the eye 3a is always sharply imaged on the photosensitive CCD array. In this manner, the camera system is in a position, by day and by night (i.e., regardless of the ambient light) to observe the eye 3a of the driver or machine operator 3 without contact and regardless of distance.

FIG. 3 shows the entire alertness determining system in block diagram form. As it can be seen therein, in this apparatus the image detection system 1, 2 is followed by an image evaluating system which has on the input end an image processing unit 6 to which the images detected by camera 1 are fed. The image evaluating system recognizes the eye via a known image processing program and causes the observation window 5 to track the eye. The image processing unit 6 operates in two states, between which it is constantly switched back and forth. In a first state, the infrared lighting 2 is turned off and the average brightness produced by the ambient light, i.e., outside light, is measured in the observation window 5. This information is output as a brightness signal 8, without the performance of any further image evaluation in this state of operation. In a second operating state, the infrared lighting 2 is turned on and the image processing unit 6 evaluates the image obtained from the observed eye according to the following criteria.

The image processing unit 6 detects the pupil diameter of the observed eye by appropriate, corresponding pupil diameter measuring means, such as those disclosed, for example, in abovementioned DE 44 19 489 A1. As mentioned, the diameter of the pupil decreases with increasing fatigue, and just before falling asleep fluctuations of the pupil diameter ranging from 0.1 Hz to 1 Hz occur. The information pertaining to the momentary pupil diameter is provided by the image evaluating unit 6, in the form of a pupil diameter signal 9. The image processing unit 6 also has conventional closed-eye detection means, whereby the length of time the eye is closed and frequency with which it closes are determined for the continuously observed eye. The image processing unit 6 provides an appropriate eye closure signal 10 which contains, on the one hand, information pertaining to the periods of time during which the eye is closed and thus no pupil diameter can be read and, on the other hand, information pertaining to the duration and frequency of closed-eye events, which is likewise, a measure of the fatigue of the person under observation.

Furthermore, the image evaluating system has an evaluating apparatus connected to the output of the image processing unit 6, which consists of a correlation unit 7 and a classification unit 11 connected thereto. The correlation unit 7 correlates the duration of the continuously measured pupil diameter (as indicated through the pupil diameter signal 9 that is fed to it) with the information pertaining to the ambient brightness obtained from the ambient brightness signal 8, so that it is able to eliminate as interference any fluctuations of the ambient brightness. The correlation unit 7 emits a corresponding correlation signal 12 which contains the information regarding the extent to which changes of pupil diameter are caused or not caused by varying ambient brightness. Additionally, the correlation unit 7 produces, by filtering the pupil diameter signal 9 in the range from 0.1 Hz to 1 Hz, a pupil diameter fluctuation signal 13 which contains information regarding whether or not fluctuations of the pupil diameter in the frequency range from 0.1 Hz to 1 Hz are caused independently of the ambient light. The correlation and filtration process in the correlation unit 7 is controlled, i.e., if the eye is closed, it is interrupted by the incoming closed-eye signal 10 and resumed when the eye is open.

The classification unit 11 performs on the basis of the closed-eye signal 10, the correlation signal 12 and the pupil diameter fluctuation signal 13 (which are fed to it), a classification which assigns the alertness state of the driver or machine operator 3 to any of four different levels, and for each level it emits a characteristic output signal 15, 16, 17, 18.

A first output signal 15 from the classification unit 11 is associated with a first level of maximum alertness which constitutes the normal state, i.e., the "awake" state of the person 3. The classification unit 11 confirms this alertness state whenever the following four conditions are satisfied. The first condition is that the pupil diameter fluctuation signal 13 is below a given pupil diameter fluctuation threshold, i.e., that no marked fluctuations of the pupil diameter are observed which are not caused by the ambient light. The second condition is that the correlation signal indicates a high correlation of the pupil diameter to the ambient light. The third condition is that the closed-eye time is less than a first pre-established closed-eye time threshold which characterizes the alertness of a person. The fourth condition is that the closed-eye frequency obtained from the closed-eye signal 10 is above a predetermined eye-closing frequency threshold, which likewise is characteristic of the alertness of a person.

A second output signal 16 from the classification unit 11 represents a "tired" state as a stage of the second-highest alertness. This stage is recognized by the classification unit 11 when the pupil size fluctuation signal 13 is lower than the threshold level of the pupil size fluctuation, and in addition at least one of three conditions is fulfilled. Namely, the correlation signal 12 indicates a lower correlation of the pupil diameter to the ambient light, the closed-eye time is above the first closed-eye time threshold which indicates that the eye has remained closed unusually long or the closed-eye frequency is below the closed-eye frequency threshold.

A third output signal 17 from the correlation unit 11 characterizes a stage of second-lowest alertness, signifying a "danger of falling asleep" condition. This state is recognized by the classification unit 11 when the pupil size fluctuation signal 13 is above the pupil size fluctuation threshold and at least one of three conditions is satisfied. These conditions are the correlation signal indicates a low correlation of the pupil diameter with the ambient light, the closed-eye time is above the first closed-eye time threshold and below the second closed-eye time threshold or the closed-eye frequency is lower than the closed-eye time threshold.

A fourth output signal 18 from the classification unit 11 corresponds to the stage of lowest alertness, which corresponds to the "eyes-shut" state. The classification unit 11 recognizes this state when the closed-eye time is above the second closed-eye time threshold level.

Following the image evaluating system is a warning unit 14 to which the four output signals 15 to 18 from the classification unit 11 are fed, and which therefore receives the information regarding the momentary state of alertness. Depending on the prevailing alertness state, the warning unit 14 performs certain actions in order to bring the vehicle or machine operator 3 back to a state of greater alertness, warn him or outsiders in due time or bring the vehicle or machine to a safe and harmless state of operation.

Thus, an optical signal 19 is provided by which the warning unit 14 can inform the person 3 under observation how tired or alert he is. Furthermore, an acoustical alarm 20 is provided by which the warning unit 14 can warn the person 3 if he becomes tired. Additionally, an operating unit 21 is provided which is operatable by the warning unit 14 such that a person 3 is required to perform a secondary task. The performance of this task feeds a message back to the operating unit 21 of the warning unit 14, after which the warning unit 14 will make any further action depend on the performance of this secondary task. Also, a transmitter 22 is provided by which the warning unit 14 can transmit the determined state of alertness to a central office or, for example, to other vehicles.

A memory 24 can be used by the warning unit 14 to record the condition of the person 3 for a specific length of time and store it to be read out. The warning unit 14 is also able to operate an automatic steering control so as to bring the vehicle or machine to a safe, harmless state of operation if necessary. This is performed by the warning unit 14 especially when the "eyes shut" state of lowest alertness is transmitted to it by the classification unit 11, or when the secondary task assigned to the operating unit 21 has been insufficiently or not performed at all by the person under observation.

The above description of an advantageous embodiment shows that the apparatus according to the invention permits a reliable determination of alertness by the combined evaluation of an eye-closed report and information pertaining to pupil size fluctuations that occur. It is evident that the apparatus according to the invention is not limited to this example, but covers additional embodiments. Thus, in addition to the described infrared light image pickup system, a system can be used which operates on other radiation, such radiation being best selected outside of the visible spectrum. Moreover, depending on the application, one or more of the components 19 to 24 controlled by the warning unit 14 can be omitted, including even the warning unit 14. Determination of alertness can be performed also in only three steps or in more than four steps according to a particular application, using modified conditions.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An apparatus for determining states of alertness of a person, comprising:
   an imaging system for imaging an area of at least one eye of the person; and
   an image evaluating system for evaluating images detected by the imaging system, said image evaluating system including
   pupil diameter determining means;
   an eye closing detection means; and
   an evaluation unit which classifies a degree of alertness of the person into one of at least three alertness stages based on eye closing information obtained by the eye closing detection means, and on pupil diameter information obtained by the pupil diameter determining means.

2. The apparatus according to claim 1, wherein:
   the image evaluating system further comprises means for determining an ambient brightness, and a correlation unit for determining a degree of correlation of the pupil diameter information to ambient brightness information obtained by the ambient brightness determining means; and
   the image evaluating system determines the state of alertness based on a degree of correlation determined by the correlation unit.

3. The apparatus according to claim 2, wherein:
   the eye closing information comprises closed-eye duration information and eye closing frequency information;
   the evaluation system outputs a highest alertness stage whenever the closed-eye duration information is below a predetermined first closed-eye duration threshold, the eye closing frequency information is above a predetermined eye closing frequency threshold and a degree of pupil diameter fluctuations not caused by the ambient brightness is below a predetermined pupil diameter fluctuation threshold; and a lowest alertness state is output when the closed-eye duration information is above a predetermined larger second closed-eye duration threshold.

4. The apparatus according to claim 3, wherein alertness intermediate stages are output by the evaluation system, a higher intermediate stage being output whenever the degree of pupil diameter fluctuations not caused by the ambient brightness is below the predetermined pupil diameter fluctuation threshold, either the closed-eye duration information is between the first closed-eye duration threshold and the larger second closed-eye duration threshold or the eye closing frequency information is below the eye closing frequency threshold, and another intermediate stage of lower alertness being output whenever the degree of pupil diameter fluctuations not caused by the ambient brightness is above the pupil diameter oscillation threshold and either the closed-eye duration information is between the first and the second closed-eye duration threshold or the eye closing frequency information is below the eye closing frequency threshold.

5. The apparatus according to claim 1, further comprising:

a warning unit operated by the image evaluating system, which emits at least one of local and remote warning signals, based on the determined state of alertness.

6. The apparatus according to claim 2, further comprising:

a warning unit operated by the image evaluating system, which emits at least one of local and remote warning signals, based on the determined state of alertness.

7. The apparatus according to claim 3, further comprising:

a warning unit operated by the image evaluating system, which emits at least one of local and remote warning signals, based on the determined state of alertness.

8. The apparatus according to claim 4, further comprising:

a warning unit operated by the image evaluating system, which emits at least one of local and remote warning signals, based on the determined state of alertness.

9. The apparatus according to claim 1, further comprising:

a warning unit operated by the image evaluating system, which operates a vehicle or machine controller;

wherein, based on the determined state of alertness, if the determined state of alertness is too low, a vehicle or machine operated by said person is brought to a safe state of operation by the warning unit.

10. The apparatus according to claim 5, further comprising:

a warning unit operated by the image evaluating system, which operates a vehicle or machine controller;

wherein, based on the determined state of alertness, if the determined state of alertness is too low, a vehicle or machine operated by said person is brought to a safe state of operation by the warning unit.

11. The apparatus according to claim 1, further comprising:

a warning unit operated by the image evaluating system; and an operating unit, operated by the warning unit, which requires performance of an alertness test by said person when an excessively low state of alertness is detected.

12. The apparatus according to claim 5, further comprising:

a warning unit operated by the image evaluating system; and an operating unit, operated by the warning unit, which requires performance of an alertness test by said person when an excessively low state of alertness is detected.

13. The apparatus according to claim 1, wherein:

the eye closing information comprises closed-eye duration information and eye closing frequency information;

the evaluation system outputs a highest alertness stage whenever the closed-eye duration information is below a predetermined first closed-eye duration threshold, the eye closing frequency information is above a predetermined eye closing frequency threshold and a degree of pupil diameter fluctuations not caused by the ambient brightness is below a predetermined pupil diameter fluctuation threshold; and a lowest alertness state is output when the closed-eye duration information is above a predetermined larger second closed-eye duration threshold.

14. The apparatus according to claim 13, wherein alertness intermediate stages are output by the evaluation system, a higher intermediate stage being output whenever the degree of pupil diameter fluctuations not caused by the ambient brightness is below the predetermined pupil diameter fluctuation threshold, either the closed-eye duration information is between the first closed-eye duration threshold and the larger second closed-eye duration threshold or the eye closing frequency information is below the eye closing frequency threshold, and another intermediate stage of lower alertness being output whenever the degree of pupil diameter fluctuations not caused by the ambient brightness is above the pupil diameter oscillation threshold and either the closed-eye duration information is between the first and the second closed-eye duration threshold or the eye closing frequency information is below the eye closing frequency threshold.

15. The apparatus according to claim 14, further comprising:

a warning unit operated by the image evaluating system, which emits at least one of local and remote warning signals, based on the determined state of alertness.

16. An apparatus for determining states of alertness of an operator of a vehicle or machines, comprising:

an imaging system for imaging an area of at least one eye of the person; and an image evaluating system for evaluating images detected by the imaging system, said image evaluating system including pupil diameter determining means;

an eye closing detection means; and an evaluation unit which classifies a degree of alertness of the person into one of at least three alertness stages based on eye closing information obtained by the eye closing detection means, and on pupil diameter information obtained by the pupil diameter determining means.

17. An apparatus for determining a state of alertness of a driver of a vehicle, comprising:

an eye closing detection unit;

an image evaluating system for evaluating images detected by the imaging system;

an imaging system for imaging an area of at least one eye of the driver, said image evaluating system including a pupil diameter determining unit; and an evaluation unit which determines the state of alertness of the driver, based on eye closing information and pupil diameter information obtained by the pupil diameter determining means;

wherein the image evaluating system classifies a degree of alertness into one of at least three alertness stages.

18. A method for determining states of alertness of a vehicle operator, comprising the steps of:

imaging an area of at least one eye of the vehicle operator using an imaging system;

evaluating images detected by the imaging system using an image evaluating system;

detecting eye closings of the vehicle operator via eye closing detection means;

determining a state of alertness based on eye closing information and pupil diameter information obtained by an evaluation unit and pupil diameter determining means, respectively; and classifying a degree of alertness into one of at least three alertness stages.

* * * * *